US010336726B2

(12) United States Patent
McMahon et al.

(10) Patent No.: US 10,336,726 B2
(45) Date of Patent: Jul. 2, 2019

(54) 3-METHYL-PYRROLIDINE-2,5-DIONE DERIVATIVES USEFUL AS CGRP RECEPTOR ANTAGONISTS

(71) Applicant: Eli Lilly and Company, Indianapolis, IN (US)

(72) Inventors: Jennifer Anne McMahon, Zionsville, IN (US); Miles Goodman Siegel, Indianapolis, IN (US); Russell Dean Stucky, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/973,681

(22) Filed: May 8, 2018

(65) Prior Publication Data
US 2018/0327384 A1   Nov. 15, 2018

Related U.S. Application Data

(60) Provisional application No. 62/506,204, filed on May 15, 2017.

(51) Int. Cl.
C07D 401/12 (2006.01)
A61K 31/4439 (2006.01)

(52) U.S. Cl.
CPC ........ C07D 401/12 (2013.01); A61K 31/4439 (2013.01); *C07B 2200/13* (2013.01)

(58) Field of Classification Search
CPC ............ C07B 2200/13; A61K 31/4439; C07D 401/12
See application file for complete search history.

(56) References Cited

U.S. PATENT DOCUMENTS

| | | | |
|---|---|---|---|
| 6,680,387 B2 | 1/2004 | Druzgala et al. | |
| 9,227,972 B2 | 1/2016 | Bell et al. | |
| 9,637,495 B2 | 5/2017 | Coates et al. | |
| 9,708,297 B2 | 7/2017 | Coates et al. | |
| 2017/0044138 A1* | 2/2017 | Coates | C07D 401/12 |

OTHER PUBLICATIONS

CAS 1390111-26-8 (Commercial Sources: Aurora Building Blocks, Order No. A20.893.332; Aurora Fine Chemicals LLC 7929 Silverton Ave., Suite 609, San Diego, CA 92126, U.S.; Aurora Screening Library Order No. K12.211.235; Aurora Fine Chemicals LLC7929 Silverton Ave., Suite 609, San Diego, CA 92126, U.S.).
CAS 1376302-01-0 (Commercial Sources: Aurora Screening Library, Order No. K11.266.151; Aurora Fine Chemicals LLC, 7929 Silverton Ave., Suite 609, San Diego, CA 92126, U.S.; Enamine HTS Collection, Order No. Z1255568116; Enamine LLC 2940 Glendale Milford Road, Suite 410, Cincinnati, OH 45241-3131, U.S.).
CAS 1573422-88-4; 4-[(2,5-dioxo-3-pyrrolidinyl)methyl]-N-[[4-[(methylamino)methyl]phenyl]methyl]-benzamide; Mar. 25, 2014; [SciFinder], [retrieved on Apr. 26, 2017]. Retrieved from the Internet <URL: https://scifinder.cas.org/scifinder/view/scifinder/scifinderExplore.isf>.
CAS 1572972-10-1; 4-[(2,5-dioxo-3-pyrrolidinyl)methyl]-N-[[4-[(methylamino)methyl]phenyl]methyl]-benzamide; Mar. 25, 2014; [SciFinder], [retrieved on Apr. 26, 2017]. Retrieved from the Internet <URL: https://scifinder.cas.org/scifinder/view/scifinder/scifinderExplore.isf>.

* cited by examiner

*Primary Examiner* — Alexander R Pagano
*Assistant Examiner* — Ebenezer O Sackey
(74) *Attorney, Agent, or Firm* — Nelson L Lentz

(57) ABSTRACT

The present invention provides a compound of Formula II:

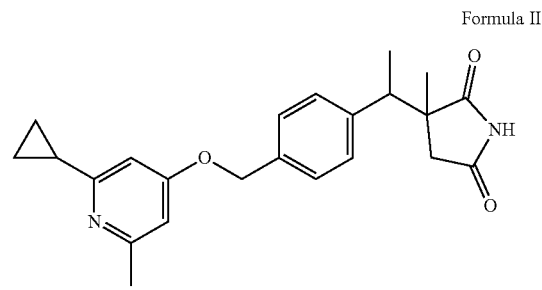

Formula II or a pharmaceutically acceptable salt or hydrate thereof, useful as a CGRP receptor antagonist.

19 Claims, No Drawings

3-METHYL-PYRROLIDINE-2,5-DIONE DERIVATIVES USEFUL AS CGRP RECEPTOR ANTAGONISTS

The present invention relates to certain novel calcitonin gene-related peptide (CGRP) receptor antagonist compounds, to pharmaceutical compositions comprising the compounds, to methods of using the compounds to prevent or treat certain physiological disorders such as migraine, and to intermediates and processes useful in the synthesis of the compounds.

The present invention is in the field of prevention and treatment of migraine and other neurological diseases and disorders thought to be mediated by CGRP (See for example, S. Benemei, et. al., *Current Opinion in Pharmacology*, 9, 9-14 (2009)). Migraine is a debilitating disease suffered by millions of people worldwide. Treatment options for migraine include the triptans, such as sumatriptan and zolmitriptan. Unfortunately, currently approved agents available to the patient do not always provide effective treatment, and these agents can be associated with various untoward side effects such as dizziness, paresthesia, and chest discomfort. In addition, triptans possess certain cardiovascular concerns causing them to be contraindicated in patients suffering from substantial underlying cardiovascular disease or uncontrolled hypertension (See T. W. Ho, et. al., *The Lancet*, 372, 2115-2123 (2008)). Thus, there is a significant unmet need in the prevention and treatment of migraine. New CGRP receptor antagonists are desired to provide treatment for or prevention of certain neurological diseases, such as migraine.

United States Publication Nos. 2017/0044138 A1 and 2017/0044163 each disclose certain CGRP receptor antagonist compounds useful in the treatment or prevention of migraine. U.S. Pat. No. 6,680,387 discloses certain 5-benzyl- or 5-benzylidene-thiazolidine-2,4-diones for the treatment of type-II diabetes mellitus, atherosclerosis, hypercholesterolemia, and hyperlipidemia.

The present invention provides certain novel compounds that are antagonists of the CGRP receptor. The present invention also provides antagonists of the CGRP receptor that are centrally penetrant.

Accordingly, the present invention provides a compound of Formula I:

Formula I or a pharmaceutically acceptable salt or hydrate thereof.

The present invention further provides a compound of Formula II:

Formula II or a pharmaceutically acceptable salt or hydrate thereof.

The present invention also provides a method of preventing migraine in a patient, comprising administering to a patient in need thereof an effective amount of a compound of Formula I or Formula II, or a pharmaceutically acceptable salt thereof.

The present invention further provides a method of treating migraine in a patient, comprising administering to a patient in need thereof an effective amount of a compound of Formula I or Formula II, or a pharmaceutically acceptable salt thereof. The present invention also provides a method of antagonizing the CGRP receptor in a patient, comprising administering to a patient in need thereof an effective amount of a compound of Formula I or Formula II, or a pharmaceutically acceptable salt thereof.

Furthermore, this invention provides a compound of Formula I or Formula II, or a pharmaceutically acceptable salt thereof for use in therapy, in particular for the treatment of migraine. In addition, this invention provides a compound of Formula I or Formula II, or a pharmaceutically acceptable salt thereof for use in preventing migraine. Even furthermore, this invention provides the use of a compound of Formula I or Formula II, or a pharmaceutically acceptable salt thereof, for the manufacture of a medicament for the treatment of migraine or for preventing migraine.

The invention further provides a pharmaceutical composition, comprising a compound of Formula I or Formula II, or a pharmaceutically acceptable salt thereof, with one or more pharmaceutically acceptable carriers, diluents, or excipients. The invention further provides a process for preparing a pharmaceutical composition, comprising admixing a compound of Formula I or Formula II, or a pharmaceutically acceptable salt thereof, with one or more pharmaceutically acceptable carriers, diluents, or excipients. This invention also encompasses novel intermediates and processes for the synthesis of the compounds of Formula I and Formula II. For example, the invention further provides the following intermediate:

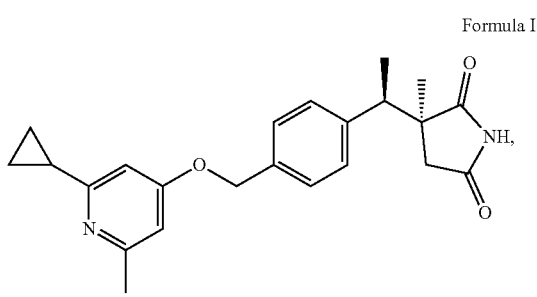 [SMILES: Cc1cc(OCc2ccc([C@@H](C)[C@]3(C)CC(=O)NC3=O)cc2)cc(C2CC2)n1]

wherein PG is a suitable protecting group. Examples of suitable protecting groups are triphenylmethyl, p-methoxybenzyl, and the like.

As used herein, the terms "treating", "treatment", or "to treat" includes restraining, slowing, stopping, or reversing the progression or severity of an existing symptom or disorder.

As used herein, the term "preventing" or "prevention" refers to protecting a patient who is prone to a certain disease or disorder, such as migraine, but is not currently suffering from symptoms of the disease or disorder, such as symptoms of migraine.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

Compounds of the present invention are effective at a dosage per day that falls within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are formulated as pharmaceutical compositions administered by any route which makes the compound bioavailable, including oral and transdermal routes. Most preferably, such compositions are for oral administration. Such pharmaceutical compositions and processes for preparing same are well known in the art (See, e.g., Remington: The Science and Practice of Pharmacy, L. V. Allen, Editor, 22$^{nd}$ Edition, Pharmaceutical Press, 2012).

The compounds of Formula I and Formula II, or pharmaceutically acceptable salts thereof are particularly useful in the prevention and treatment methods of the invention, but certain configurations are preferred. The following paragraphs describe such preferred configurations. Although the present invention contemplates all individual enantiomers and diasteromers, as well as mixtures of the enantiomers of said compounds, including racemates, the compounds with absolute configuration as set forth below are especially preferred. It is understood that these preferences are applicable both to the prevention and treatment methods and to the new compounds of the invention.

The following compounds are preferred:

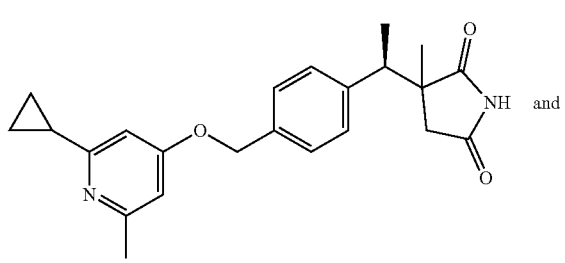 and

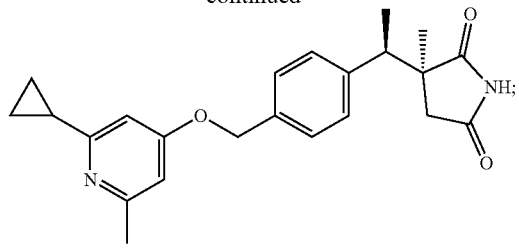

and the pharmaceutically acceptable salts and hydrates thereof.

The following compound is more preferred:

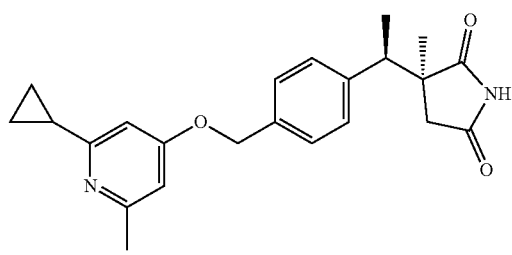 [SMILES: Cc1cc(OCc2ccc([C@@H](C)[C@]3(C)CC(=O)NC3=O)cc2)cc(C2CC2)n1]

and the pharmaceutically acceptable salts thereof.

The following compounds are especially preferred:
(3S)-3-[(1R)-1-[4-[(2-cyclopropyl-6-methyl-4-pyridyl)oxymethyl]phenyl]ethyl]-3-methyl-pyrrolidine-2,5-dione;
(3S)-3-[(1R)-1-[4-[(2-cyclopropyl-6-methyl-4-pyridyl)oxymethyl]phenyl]ethyl]-3-methyl-pyrrolidine-2,5-dione hydrochloride;
(3S)-3-[(1R)-1-[4-[(2-cyclopropyl-6-methyl-4-pyridyl)oxymethyl]phenyl]ethyl]-3-methyl-pyrrolidine-2,5-dione hydrobromide;
(3S)-3-[(1R)-1-[4-[(2-cyclopropyl-6-methyl-4-pyridyl)oxymethyl]phenyl]ethyl]-3-methyl-pyrrolidine-2,5-dione hydrobromide monohydrate; and
(3S)-3-[(1R)-1-[4-[(2-cyclopropyl-6-methyl-4-pyridyl)oxymethyl]phenyl]ethyl]-3-methyl-pyrrolidine-2,5-dione hydrochloride monohydrate.

Certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See, for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

A pharmaceutically acceptable salt of the compounds of the invention can be formed, for example, by reaction of an appropriate free base of a compound of the invention, an appropriate pharmaceutically acceptable acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "ACN" refers to acetonitrile; "c-Pr" refers to cyclopropyl; "DCM" refers to DCM or methylene chloride; "DMEA" refers to N,N-dimethylethylamine; "DIPEA" refers to N,N-diisopropylethylamine; "DMF" refers to N,N-dimethylformamide; "DMSO" refers to dimethylsulfoxide; "Et" refers to ethyl; "Et$_2$O" refers to diethyl ether; "EtOAc" refers to ethyl acetate; "EtOH" refers to ethanol; "g" when used in reference to centrifugation, refers to relative centrifugal force; "HPLC" refers to high Performance Liquid Chromatography; "HOBt" refers to hydroxybenzotriazole; "hr" refers to hour or hr; "HATU" refers to 1-[Bis(dimethylamino)methylene]-1H-1,2,3-triazolo[4,5-b]pyridinium 3-oxide hexafluorophosphate or N-[(dimethylamino)-1H-1,2,3-triazolo-[4,5-b]pyridin-1-ylmethylene]-N-methylmethanaminium hexafluorophosphate N-oxide; "HTRF" refers to Homogeneous Time Resolved Fluorescence; "IC$_{50}$" refers to the concentration of an agent that produces 50% of the maximal inhibitory response possible for that agent; "kPa" refers to kilopascal or kilopascals; "kV" refers to kilovolts; "LAH" refers to lithium aluminum hydride; "LC-ES/MS" refers to Liquid Chromatography Electrospray Mass Spectrometry; "LDA" refers to lithium diisopropylamide; "mA" refers to milliamps or milliamperes; "MDCK" refers to Madin-Darby canine kidney epithelial cells; "min" refers to minute or minutes; "Me" refers to methyl; "MeOH" refers to methanol or methyl alcohol; "MTBE" refers to methyl-tert-butyl ether; "NaHMDS" refers to sodium bis(trimethylsilyl) amide; "n-BuLi" refers to n-butyllithium; "psi" refers to pounds per square inch; "rpm" refers to revolutions per minute; "RT" refers to room temperature; "SEM" refers to standard error of the mean; "SFC" refers to Supercritical Fluid Chromatography; "T3P" refers to 2,4,6-tripropyl-1,3,5,2,4,6-trioxatriphosphorinane-2,4,6-trioxide solution; "t-BuOH" refers to tert-butanol; "TEA" refers to triethylamine; "TFA" refers to trifluoroacetic acid; "THF" refers to tetrahydrofuran; "TMEDA" refers to tetrametylethylenediamine; "t$_R$" refers to retention time; "U/mL" refers to units per milliliter.

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The following schemes, preparations, examples, and assays further illustrate the invention, but should not be construed to limit the scope of the invention in any way.

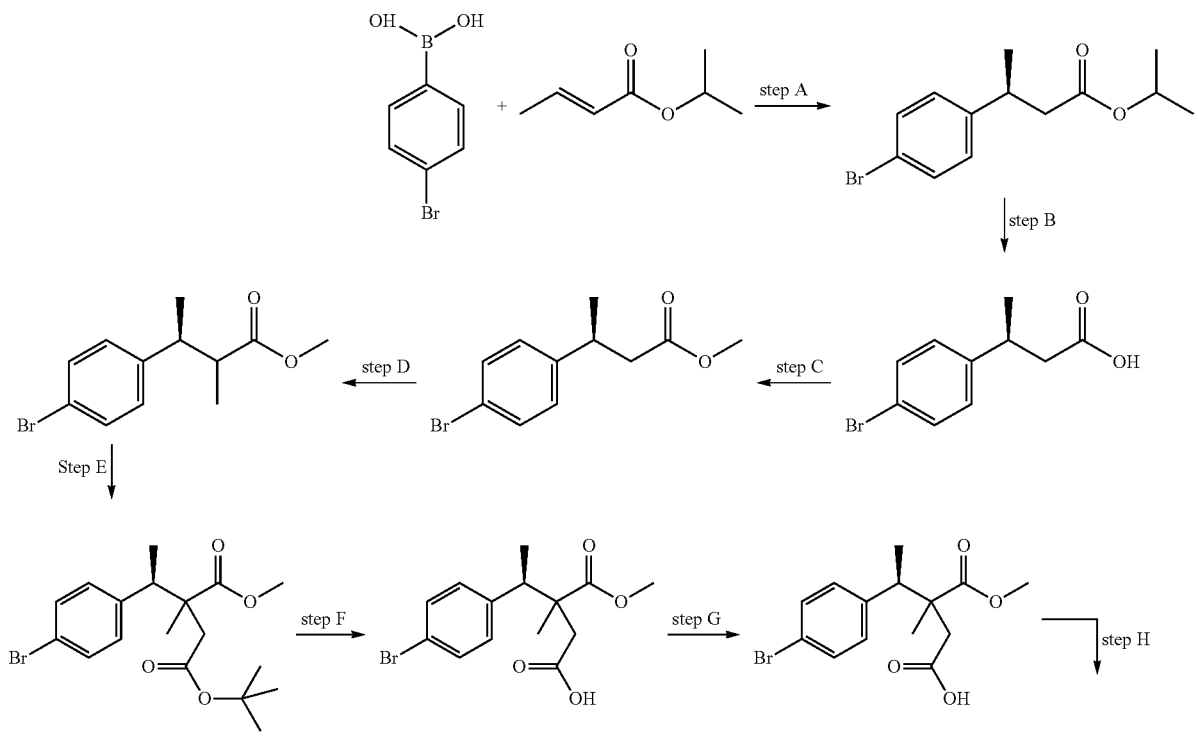

Scheme 1

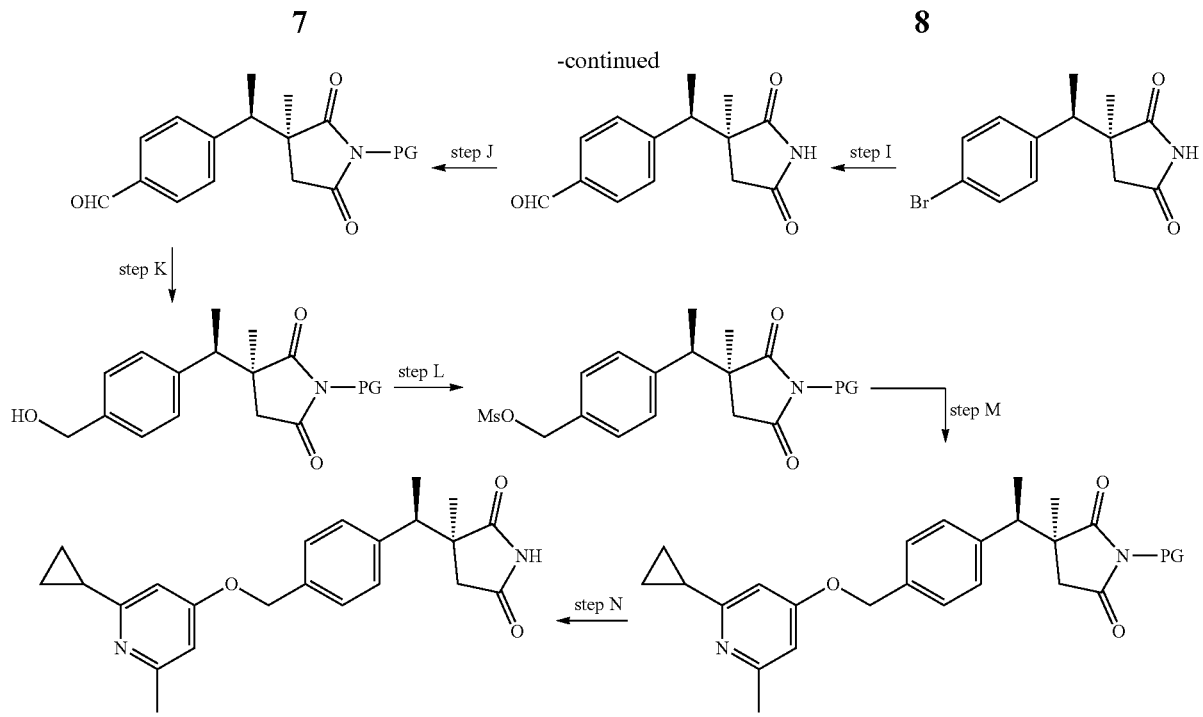

Scheme 1 depicts the synthesis of (3S)-3-[(1R)-1-[4-[(2-cyclopropyl-6-methyl-4-pyridyl)oxymethyl]phenyl]ethyl]-3-methyl-pyrrolidine-2,5-dione. In Scheme 1, step A, asymmetric arylation of isopropyl (E)-but-2-enoate may be accomplished under coupling conditions using transition-metal catalysts, such as rhodium, as is well-described in the art. Generally, an aryl boronic acid may be coupled to isopropyl (E)-but-2-enoate to yield rhodium catalysis product isopropyl (3S)-3-(4-bromophenyl)butanoate with high enantioselectivity. For example, about 1.05-1.1 equivalents of 4-bromophenyl boronic acid may be treated with about 0.01 equivalents of a rhodium catalyst, specifically, bis(norbornadiene)rhodium(I) tetrafluoroborate, followed by addition of an appropriate chiral ligand such as 0.01-0.015 equivalents (R)-(+)-2,2'-bis(diphenylphosphino)-1,1'-binaphthyl, about 1 equivalent TEA, and about 1 equivalent of isopropyl (E)-but-2-enoate in an appropriate solvent mixture such as wet 1,4-dioxane or THF and water (about 8:1). The resulting reaction mixture may be heated to about 40° C. for about 18 hr. The product can then be isolated and purified utilizing techniques well known in the art, such as extraction methods and chromatography. For example, the reaction mixture may be diluted with water and extracted with an appropriate nonpolar organic solvent such as MTBE or DCM. The organic extracts may be combined, dried over anhydrous $Na_2SO_4$, filtered, and concentrated under reduced pressure to provide the crude product of step A. The crude product may then be purified by flash chromatography on silica gel with a suitable eluent, such as hexanes/EtOAc gradient, to provide the purified product of step A, isopropyl (3S)-3-(4-bromophenyl)butanoate in high enantiomeric excess.

In Scheme 1, step B, hydrolysis of the product from Scheme 1, step A, may be accomplished under saponification conditions well known in the art. For example, isopropyl (3S)-3-(4-bromophenyl)butanoate may be dissolved in an appropriate alcoholic solvent such as MeOH and treated with an excess of aqueous mineral base such as NaOH. After heating for about 1 hr, the product can then be isolated and purified utilizing techniques well known in the art, such as extraction, trituration, and evaporation methods. For example, the reaction mixture may be extracted with an appropriate organic solvent such as DCM and the resulting separated aqueous layer may be treated with an excess of a mineral acid such as conc. HCl to pH~4. The acidified aqueous layers may then be extracted with an appropriate organic solvent such as DCM. The organic extracts may be combined, dried over anhydrous $Na_2SO_4$, filtered, and concentrated under reduced pressure to provide the crude product of step B. The crude product may be triturated with a non-polar organic solvent such as heptanes, the resulting precipitates may be filtered away, and the filtrate may be concentrated under reduced pressure to obtain the product of step B, (3S)-3-(4-bromophenyl)butanoic acid, in very high enantiomeric excess.

In Scheme 1, step C, esterification of the product from Scheme 1 step B, may be carried out under a wide range of acidic/basic esterification methods well known in the art, or by direct esterification with diazomethane. For example, (3S)-3-(4-bromophenyl)butanoic acid dissolved in an appropriate alcoholic solvent such as MeOH may be treated with an excess of a mineral acid, such as conc. $H_2SO_4$. The resulting mixture may be heated for about 2 hr, and the product can then be isolated by utilizing techniques well known in the art, such as extraction. The reaction mixture may be concentrated under reduced pressure, and the resulting residue may be partitioned between water and a suitable organic solvent such as MTBE. The organic extracts may be combined, washed with water, dried over anhydrous $MgSO_4$, filtered, and concentrated under reduced pressure to provide the product of step C, methyl (3S)-3-(4-bromophenyl)butanoate, suitable for use without additional purification.

In Scheme 1, step D, alkylation of the product of scheme 1 step C, may be achieved using variety of alkylation conditions well known in the literature. For example, methylation of methyl (3S)-3-(4-bromophenyl)butanoate may be accomplished by treatment with about 1.5-1.75 equivalents of a non-nucleophilic base such as n-BuLi in an appropriate solvent such as anhydrous THF at low temperature followed by quenching of the resulting anion with about 1.5-1.6 equivalents $CH_3I$. The product can then be isolated by utilizing techniques well known in the art, such as extraction. The reaction mixture may be partitioned between water and an appropriate organic solvent such as MTBE. The combined organic extracts may be washed sequentially with water, saturated aqueous NaCl, dried over $MgSO_4$, filtered, and concentrated under reduced pressure to obtain the product of step D, (3S, 2R/S)-methyl 3-(4-bromophenyl)-2-methylbutanoate, as a mixture of diastereomers suitable for use without additional purification.

In Scheme 1, step E, the product of Scheme 1 step D, (3S, 2R/S)-methyl 3-(4-bromophenyl)-2-methylbutanoate as a mixture of diastereomers, may be treated with about 1 equivalent of an organic base such as n-butyllithium in an appropriate organic solvent such as anhydrous THF at low temperature. The resulting mixture may then be treated with a solution of about 0.9 equivalents tert-butyl 2-bromoacetate. The product can then be isolated by utilizing techniques well known in the art, such as extraction. The reaction mixture may be partitioned between water and an appropriate organic solvent such as MTBE, and the combined organic extracts may be washed sequentially with water and saturated aqueous NaCl. The organic extracts may be dried over $MgSO_4$, filtered, and concentrated under reduced pressure to obtain the product of step E, 4-(tert-butyl) 1-methyl (S/R)-2-((R)-1-(4-bromophenyl)ethyl)-2-methylsuccinate, as a mixture of diastereomers suitable for use without additional purification.

In Scheme 1, step F, a mixture of the diastereomeric esters from the product of Scheme 1 step E, may be hydrolyzed under conditions well known in the prior art. For example, 4-(tert-butyl) 1-methyl (S/R)-2-((R)-1-(4-bromophenyl) ethyl)-2-methylsuccinate may be dissolved in an appropriate organic solvent such as DCM and treated with an excess or an organic acid such as TFA. The resulting mixture may be stirred at RT for about 18 hr, and the product can then be isolated by utilizing techniques well known in the art, such as extraction. The reaction mixture may be washed sequentially with water and saturated aqueous NaCl, the organic extracts may be dried over $MgSO_4$, filtered and concentrated under reduced pressure to obtain the product of step F, (3S/R,4R)-4-(4-bromophenyl)-3-(methoxycarbonyl)-3-methylpentanoic acid, as a mixture of diastereomers suitable for use without additional purification.

In Scheme 1, step G, a mixture of the diastereomers from Scheme 1 step F, (3S/R,4R)-4-(4-bromophenyl)-3-(methoxycarbonyl)-3-methylpentanoic acid, may be dissolved in an appropriate polar organic solvent such as anhydrous DMF and treated sequentially with a non-nucleophilic base such as about 3 equivalents of TEA or DIPEA, about 1.2 equivalents of an amide coupling reagent such as HATU, and a solution of excess methanolic ammonia. The resulting mixture may be stirred at RT for about 2-12 hr, and the product can then be isolated by utilizing techniques well known in the art, such as extraction. The reaction mixture may be partitioned between water and an appropriate organic solvent such as DCM, the layers may be separated, and the combined organic extracts are washed sequentially with water and saturated aqueous NaCl. The extracts may then be dried over $MgSO_4$, filtered, and concentrated under reduced pressure to obtain the product of step G, methyl (2S/R)-4-amino-2-[(1R)-1-(4-bromophenyl)ethyl]-2-methyl-4-oxo-butanoate, as a mixture of diastereomers suitable for use without additional purification.

In Scheme 1, step H, a mixture of the diastereomeric product of Scheme 1 step G may be cyclized by heating in the presence of a non-nucleophilic base followed by separation of diastereomers under chiral chromatography conditions. For example, methyl (2S/R)-4-amino-2-[(1R)-1-(4-bromophenyl)ethyl]-2-methyl-4-oxo-butanoate may be dissolved in a mixture of THF/water (about 1:1), treated with about 2.5 equivalents of a non-nucleophilic base such as sodium carbonate, and the resulting mixture may be heated to about 60° C. for about 2 hr. The product can then be isolated by utilizing techniques well known in the art, such as extraction followed by separation of the diastereomers under chiral chromatography conditions. For example, the reaction mixture is extracted with EtOAc, the combined organic extracts are dried over $MgSO_4$, filtered, and concentrated under reduced pressure to give a crude mixture of diastereomers. The diastereomers may be separated by chiral SFC technology, using an isocratic solvent system of EtOH containing a small amount of a non-nucleophilic amine such as N,N-diethylmethylamine/$CO_2$ (about 1:9) to obtain the separated products of step H, (3S)-3-[(1R)-1-(4-bromophenyl)ethyl]-3-methyl-pyrrolidine-2,5-dione and (3R)-3-[(1R)-1-(4-bromophenyl)ethyl]-3-methyl-pyrrolidine-2,5-dione.

In Scheme 1, step I, the product of step H may be carbonylated under conditions well described in the art. For example, about 1 equivalent of (3S)-3-[(1R)-1-(4-bromophenyl)ethyl]-3-methyl-pyrrolidine-2,5-dione may be heated with about 0.03-0.04 equivalents of a transitional-metal reagent such as palladium(II) acetate, about 0.10-0.15 equivalents of a suitable phosphine ligand reagent such as butyl-di-1-adamantyl-phosphine, and slight excess of a non-nucleophilic base, such as TMEDA, in a suitable non-polar organic solvent such as toluene, in a sealed reaction vessel pressurized to about 75 psi under an atmosphere of carbon monoxide/hydrogen. The resulting mixture may be heated for about 16 hr at about 95° C., then cooled to RT, filtered over a bed of diatomaceous earth, and concentrated under reduced pressure. The product may then be isolated by utilizing techniques well known in the art, such as chromatography. For example, the crude residue obtained after solvent evaporation can be purified by flash chromatography on silica, eluting with a suitable organic solvent mixture, such as hexanes/ethyl acetate, to provide the product of step I, 4-[(1R)-1-[(3S)-3-methyl-2,5-dioxo-pyrrolidin-3-yl] ethyl]benzaldehyde.

The succinimide nitrogen of 4-[(1R)-1-[(3S)-3-methyl-2,5-dioxo-pyrrolidin-3-yl]ethyl]benzaldehyde may be protected with a suitable protecting group "PG" under conditions well known in the art, as shown in Scheme 1, step J. For example, for PG=trityl, about 1 equivalent of 4-[(1R)-1-[(3S)-3-methyl-2,5-dioxo-pyrrolidin-3-yl]ethyl]-benzaldehyde, the product of Scheme 1, step I, may be treated with about 1.5 equivalents of an appropriate base, such as $Cs_2CO_3$, and about 1.2 equivalents of triphenylmethyl chloride, in a suitable polar organic solvent such as DMF at RT for about 4-6-hr. The product may be isolated by utilizing techniques well known in the art, such as extraction methods and chromatography. For example, the crude reaction mixture may be diluted with water, extracted with a suitable organic solvent, such as DCM or EtOAc, the resulting layers may be separated, and the organic extracts may be washed with saturated aqueous NaCl, dried over $Na_2SO_4$, filtered, and concentrated under reduced pressure. The resulting crude product may be purified by flash chromatography over silica gel, eluting with a suitable organic solvent mixture, such as hexanes/ethyl acetate, to provide the product of step J, 4-[(1R)-1-[(3S)-3-methyl-2,5-dioxo-1-trityl-pyrrolidin-3-yl]ethyl]benzaldehyde.

In Scheme 1, step K, the N-protected benzaldehyde product of Scheme 1, step J, may be reduced under a wide array of conditions well-described in the art. For example, about 1 equivalent of 4-[(1R)-1-[(3S)-3-methyl-2,5-dioxo-1-trityl-pyrrolidin-3-yl]ethyl]-benzaldehyde, the product of Scheme 1, step J, may be suspended in a suitable alcoholic solvent, such as EtOH, or dissolved in a suitable polar organic solvent, such as THF or 1,4-dioxane, and treated with about 1.5 equivalents of sodium borohydride, either all in one portion, or added portion-wise, at about 0° C. for about 30-60 min. The product may be isolated by utilizing techniques well known in the art, such as extraction methods and chromatography. The crude reaction mixture may be diluted with water, extracted with a suitable polar organic solvent, such as EtOAc, the resulting layers may be separated, and the organic extracts may be washed with saturated aqueous NaCl, dried over $Na_2SO_4$, filtered, and concentrated under reduced pressure. The resulting crude product may be purified by flash chromatography over silica gel, eluting with a suitable organic solvent mixture, such as hexanes/ethyl acetate, to provide the product of step K, (3S)-3-[(1R)-1-[4-(hydroxymethyl)phenyl]ethyl]-3-methyl-1-trityl-pyrrolidine-2,5-dione.

In Scheme 1, step L, the alcohol product of Scheme 1, step K may be converted to a suitable leaving group, such as an alkyl halide, alkyl mesylate, or alkyl tosylate, under an array of conditions well known in the art. For example, about 1 equivalent of (3S)-3-[(1R)-1-[4-(hydroxymethyl)phenyl]ethyl]-3-methyl-1-trityl-pyrrolidine-2,5-dione, the product of Scheme 1, step K, may be dissolved in a suitable organic solvent, such as DCM, cooled to about 0° C., and treated sequentially with about 1.5 equivalents of an appropriate non-nucleophilic base, such as TEA, and about 1.2 equivalents methane sulfonyl chloride. The product may be isolated by utilizing techniques well known in the art, such as extraction methods. The reaction mixture may be diluted with water and DCM, the resulting layers separated, and the organic extract may be washed sequentially with saturated aqueous $NaHCO_3$ and saturated aqueous NaCl, dried over $Na_2SO_4$, filtered, and concentrated under reduced pressure, to obtain the crude product of step L, [4-[(1R)-1-[(3S)-3-methyl-2,5-dioxo-1-trityl-pyrrolidin-3-yl]ethyl]phenyl]methyl methanesulfonate, of sufficient purity for subsequent use without additional purification.

The product of Scheme 1, step L, may be treated with various nucleophiles under a wide array of conditions well described in the art. For example, in Scheme 1, step M, a solution of about 1 equivalent of (3S)-3-[(1R)-1-[4-[(2-cyclopropyl-6-methyl-4-pyridyl)-oxymethyl]phenyl]ethyl]-3-methyl-1-trityl-pyrrolidine-2,5-dione in an appropriate polar organic solvent, such as DMF, may be added to a slurry of about 0.75-0.95 equivalents of 2-cyclopropyl-6-methyl-pyridin-4-ol and about 0.75-0.95 equivalents NaH or NaH-MDS, in a suitable organic solvent, such as DMF or ACN, at about 0° C. to RT. The resulting mixture may be stirred for about 16 hr, and the product may be isolated by utilizing techniques well known in the art, such as extraction methods and chromatography. The reaction mixture may be diluted with water, extracted with a suitable polar organic solvent, such as EtOAc, the layers separated, and the organic extract may be washed with saturated aqueous NaCl, dried over $Na_2SO_4$, filtered, and concentrated under reduced pressure. The resulting crude product may be purified by flash chromatography over silica gel, eluting with a suitable organic solvent mixture, such as hexanes/ethyl acetate, to provide the product of step M, (3S)-3-[(1R)-1-[4-[(2-cyclopropyl-6-methyl-4-pyridyl)oxymethyl]phenyl]ethyl]-3-methyl-1-trityl-pyrrolidine-2,5-dione.

Scheme 1, step N depicts the deprotection of the succinimide nitrogen, which may be accomplished under a wide array of conditions specific to the protecting group, as is well known in the art. For example, when PG=trityl, about 1 equivalent of (3S)-3-[(1R)-1-[4-[(2-cyclopropyl-6-methyl-4-pyridyl)oxymethyl]phenyl]ethyl]-3-methyl-1-trityl-pyrrolidine-2,5-dione, the product of Scheme 1, step M, may be dissolved in a suitable organic solvent, such as DCM, and treated with excess TFA for about 12-24 hr. The reaction mixture may be adjusted to pH~6 with an aqueous solution of 1N NaOH. The product may be isolated by utilizing techniques well known in the art, such as extraction methods and chromatography. The reaction mixture may be diluted with water, extracted with DCM, the layers separated, and the organic extract may be washed with saturated aqueous NaCl, dried over $Na_2SO_4$, filtered, and concentrated under reduced pressure. The resulting crude product can be purified by flash chromatography over silica gel, eluting with an appropriate solvent mixture, such as MeOH in DCM, to obtain the product of step N, (3S)-3-[(1R)-1-[4-[(2-cyclopropyl-6-methyl-4-pyridyl)oxymethyl]phenyl]ethyl]-3-methyl-pyrrolidine-2,5-dione.

Scheme 2

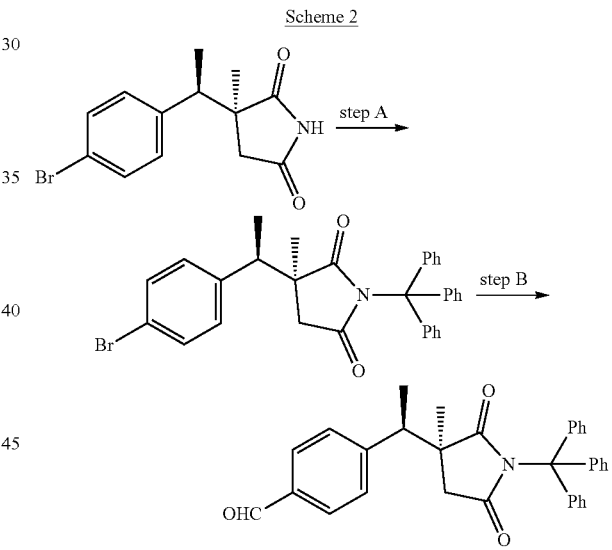

Scheme 2 depicts the synthesis of 4-[(1R)-1-[(3S)-3-methyl-2,5-dioxo-1-trityl-pyrrolidin-3-yl]ethyl]benzaldehyde. In Scheme 2, step A, the succinimide nitrogen of (3S)-3-[(1R)-1-(4-bromophenyl)ethyl]-3-methyl-pyrrolidine-2,5-dione, which is the product of Scheme 1, step H, may be protected by tritylation in a manner essentially analogous to the procedure described in Scheme 1, step J. For example, about 1 equivalent (3S)-3-[(1R)-1-(4-bromophenyl)ethyl]-3-methyl-pyrrolidine-2,5-dione may be treated with about 1.5 equivalents of an appropriate base, such as $Cs_2CO_3$, and about 1.2 equivalents of triphenylmethyl chloride, in a suitable polar organic solvent such as DMF at RT for about 4 hr. The product may be isolated by utilizing techniques well known in the art, such as filtration. For example, the reaction mixture can be diluted with water and cooled to about 0° C. The resulting precipitate may be collected by filtration, reconstituted in hot MeOH, cooled to RT, and the resulting precipitate collected by filtration to obtain the product of step A, (3S)-3-[(1R)-1-(4-bromophenyl)ethyl]-3-methyl-1-trityl-pyrrolidine-2,5-dione. In Scheme 2, step B, this material may be carbonylated in a manner essentially analogous to the procedure described in Scheme 1, step I, to provide 4-[(1R)-1-[(3S)-3-methyl-2,5-dioxo-1-trityl-pyrrolidin-3-yl]ethyl]benzaldehyde. Subsequent reduction, conversion to the mesylate, etherification with 2-cyclopropyl-6-methyl-pyridin-4-ol, and deprotection all as described in Scheme 1, steps K-N may provide (3S)-3-[(1R)-1-[4-[(2-cyclopropyl-6-methyl-4-pyridyl)oxymethyl]phenyl]ethyl]-3-methyl-pyrrolidine-2,5-dione.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R- or S-configuration of the compound of the invention may be determined by standard techniques such as X-ray analysis and correlation with chiral-HPLC retention time.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 µm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparative reversed phase chromatography is performed on an AGILENT® 1200 LC-ES/MS equipped with a Mass Selective Detector mass spectrometer and a LEAP® autosampler/fraction collector. High pH methods are run on a 75×30 mm PHENOMENEX® GEMINI®-NX, 5µ particle size columns with a 10×20 mm guard. Flow rate of 85 mL/min. Eluent is 10 mM ammonium bicarbonate (pH 10) in acetonitrile.

NMR spectra are performed on a Bruker AVIII HD 400 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1

Isopropyl (3S)-3-(4-bromophenyl)butanoate

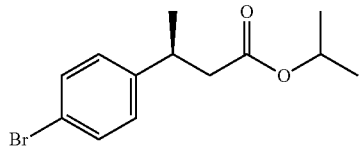 [SMILES: CC(C)OC(=O)C[C@H](C)c1ccc(Br)cc1]

Scheme 1, step A: To a deoxygenated solution of (4-bromophenyl)boronic acid (110 g, 547.73 mmol) in 1,4-dioxane (750 mL) under N$_2$ atmosphere is added bis(norbornadiene)rhodium(I) tetrafluoroborate (2 g, 5.13 mmol) followed by (R)-(+)-2,2'-bis(diphenylphosphino)-1,1'-binaphthyl (4.5 g, 7.2 mmol). The mixture is aged at room temperature for 1 hr before adding H$_2$O (100 mL), TEA (70 mL, 502 mmol), and isopropyl (E)-but-2-enoate (65 g, 507.14 mmol). The resulting red solution is heated to 40° C. for 18 hr. The reaction mixture is concentrated under reduced pressure to half volume and diluted with 500 mL MTBE. The organic solution is washed with 500 mL water, dried over Na$_2$SO$_4$, filtered, and concentrated to dryness under reduced pressure. The crude product is purified by flash chromatography on silica, eluting with hexanes/EtOAc (gradient from 1:0 to 9:1). The pure chromatography fractions are combined and concentrated under reduced pressure to give the title compound (144 g, 94.6% yield, 94.5% ee). Major enantiomer t$_R$=2.20 min; minor enantiomer t$_R$=2.69 min (Chiral SFC Lux Amylose-2, 5% MeOH/CO$_2$, 5 mL/min, 225 nm). $^1$H NMR (DMSO-d$_6$): δ 1.05 (d, J=6.2 Hz, 3H), 1.10 (d, J=6.2 Hz, 3H), 1.19 (d, J=7.0 Hz, 3H), 2.48-2.59 (m, 2H), 3.08-3.19 (m, 1H), 4.74-4.84 (m, 1H), 7.20-7.24 (m, 2H), 7.44-7.48 (m, 2H).

Preparation 2

(3S)-3-(4-bromophenyl)butanoic Acid

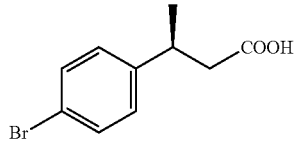

Scheme 1, step B: To a solution of isopropyl (3S)-3-(4-bromophenyl)butanoate (1042 g, 3471.0 mmol) in MeOH (8 L) is added 5 M aqueous NaOH (2 L) while stirring at RT. The reaction is heated to 50° C. under N$_2$ atmosphere for 40 min. After cooling down to 30° C., the reaction mixture is concentrated under reduced pressure and the residue is diluted with 2 L water. The resulting aqueous mixture is extracted once with DCM (~2 L). The aqueous layer is treated with ~1 kg of ice and acidified to pH~4 with conc. HCl (1 L) by slow addition over the course of 20 min. The cloudy aqueous layer is then extracted with DCM (~4 L). The organic layer is dried over Na$_2$SO$_4$, filtered, and concentrated under reduced pressure to a clear tan oil which solidified to an off-white solid. Heptane (~4 L) is added to the solid and the resulting mixture is heated to 45° C. for 2 hr upon which a solid precipitates. The solids are collected by filtration and washed with heptane (200-250 mL). The filtrate is then concentrated to dryness under reduced pressure to give the title compound as an off-white solid (771 g, 91.4% yield, 99% ee). ES/MS (m/z): 241.0 (M−H). Major enantiomer $t_R$=2.35 min; minor enantiomer $t_R$=2.82 min (Chiral SFC Lux Amylose-2, 5% MeOH/CO$_2$, 5 mL/min, 225 nm). $^1$H NMR (DMSO-d$_6$): δ 1.19 (d, J=7.0 Hz, 3H), 2.48-2.52 (m, 2H), 3.07-3.17 (m, 1H), 7.20-7.25 (m, 2H), 7.44-7.49 (m, 2H), 12.08 (s, 1H). $[α]_D^{25}$+25.0° (c=1, MeOH).

Preparation 3 methyl (3S)-3-(4-bromophenyl)butanoate

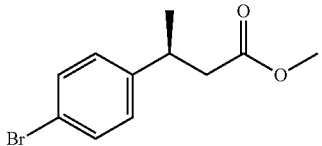

Scheme 1, step C: Concentrated H$_2$SO$_4$ (45 mL, 802 mmol) is added to a solution of (3S)-3-(4-bromophenyl) butanoic acid (450 g, 1851.1 mmol) in MeOH (4.5 L). The mixture is heated at 65° C. for 2 h, cooled to RT, and concentrated under reduced pressure to a dry residue. The solid is diluted with MTBE (2.5 L) and H$_2$O (2.5 L) and the resulting mixture is extracted with MTBE (2×2.5 L). The combined extracts are washed with H$_2$O (2.5 L), dried over MgSO$_4$, filtered, and concentrated under reduced pressure to give the title compound as a light yellow oil (469.8 g, >99% yield) that may be used without further purification. ES/MS (m/z): 274.0 (M+NH$_4^+$). $^1$H NMR (CDCl$_3$): δ 1.27 (d, J=7.0 Hz, 3H), 2.50-2.62 (m, 2H), 3.20-3.30 (m, 1H), 3.61 (s, 3H), 7.07-7.12 (m, 2H), 7.39-7.43 (m, 2H).

Preparation 4

(3S, 2R)-methyl 3-(4-bromophenyl)-2-methylbutanoate and (3S, 2S)-methyl 3-(4-bromophenyl)-2-methylbutanoate

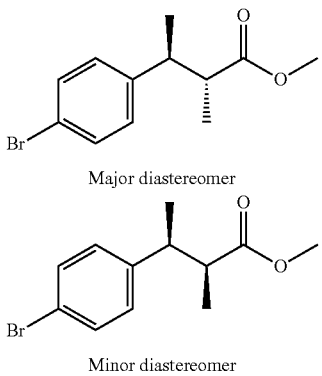

Scheme 1, step D: A 2.5 M solution of n-BuLi in hexanes (1250 mL) is added drop wise to a solution of DIPEA (444 mL, 3150 mmol) in anhydrous THF (2.3 L) at −40° C. over 30 min. After 30 min, a solution of methyl (3S)-3-(4-bromophenyl)butanoate (468.90 g, 1750.7 mmol) in anhydrous THF (3.3 L) is added over 40 min, and the reaction mixture is aged for 40 min at −40° C. CH$_3$I (176 mL, 2798 mmol) is added over 30 min and the mixture is stirred for 15 min at −40° C. The reaction mixture is quenched slowly at −40° C. with MeOH (283 mL) followed by H$_2$O (2.5 L) and the mixture is allowed to warm to RT. The reaction mixture is diluted with H$_2$O (2.5 L) and the resulting layers are separated. The aqueous layer is additionally extracted with MTBE (7.5 L) and the combined organic extracts are washed sequentially with H$_2$O (3 L) and saturated aqueous NaCl (2.5 L). The organic extracts are dried over MgSO$_4$, filtered, and concentrated under reduced pressure to give the title compound as a mixture of diastereomers (7:3) as a light brown oil (489 g, 93% yield) that may be used without further purification. Major diastereomer $t_R$=1.29 min; minor diastereomer $t_R$=1.32 min (XBRIDGE® C18 column, 3.5μ, 2.1×50 mm, 1.2 mL/min, 50° C., 10-95% 10 mM NH$_4$CO$_3$ (pH 10) in ACN). ES/MS (m/z for $^{79}$Br/$^{81}$Br): 288.0, 290.0 (M+NH$_4^+$).

Preparation 5

4-(tert-butyl) 1-methyl (S)-2-((R)-1-(4-bromophenyl)ethyl)-2-methylsuccinate and 4-(tert-butyl) 1-methyl (R)-2-((R)-1-(4-bromophenyl)ethyl)-2-methylsuccinate

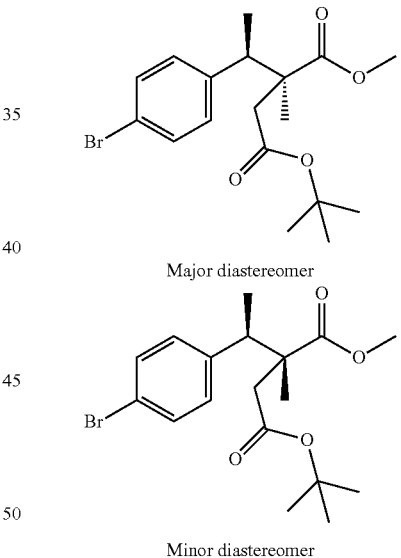

Scheme 1, step E: A 2.5 M solution of n-BuLi in hexanes (1150 mL, 2900 mmol) is added over 20 min to a solution of DIPEA (410 mL, 2910 mmol) in anhydrous THF (3 L) at −40° C. The resulting mixture is stirred at −40° C. for 30 min, and a solution of a mixture of diastereomers methyl (2R/S,3S)-3-(4-bromophenyl)-2-methyl-butanoate (488.00 g, 1619.8 mmol) in anhydrous THF (3 L) is added over a period of 1 hr. The reaction mixture is aged for 45 min at −40° C., and a solution of tert-butyl 2-bromoacetate (391 mL, 2596 mmol) in anhydrous THF (250 mL) is added over 30 min. The resulting mixture is stirred for an additional 30 min at −40° C. MeOH (250 mL) is added followed by H$_2$O (2.5 L), and the resulting mixture is allowed to warm to RT. The mixture is diluted with H$_2$O (2.5 L) and the resulting layers are separated. The aqueous layer is extracted with MTBE (5 L), and the organic extract is washed sequentially with H$_2$O (5 L) followed by saturated aqueous NaCl (2.5 L), dried over MgSO$_4$, filtered, and concentrated under reduced pressure to give the title compound as a mixture of diastereomers as a thick brown oil (786 g, 87% yield) that may be used without further purification. Major diastereomer t$_R$=1.51 min; minor diastereomer t$_R$=1.53 min (XBRIDGE® C18 column, 3.5μ, 2.1×50 mm, 1.2 mL/min, 50° C., 10-95% 10 mM NH$_4$CO$_3$ (pH 10) in ACN). ES/MS (m/z for $^{79}$Br/$^{81}$Br): 328.8, 330.8 (M-tBu+H).

Preparation 6

(3S,4R)-4-(4-bromophenyl)-3-(methoxycarbonyl)-3-methylpentanoic Acid and (3R,4R)-4-(4-bromophenyl)-3-(methoxycarbonyl)-3-methylpentanoic Acid

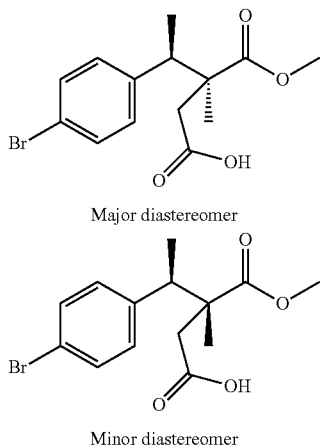

Major diastereomer

Minor diastereomer

Scheme 1, step F: A solution of a mixture of diastereomers 4-(tert-butyl) 1-methyl (R/S)-2-((R)-1-(4-bromophenyl)ethyl)-2-methylsuccinate (785 g, 1406 mmol) in DCM (6 L) is treated with TFA (1.06 L) and stirred at RT for 18 hr. The reaction mixture is washed sequentially with H$_2$O (2×5 L) and saturated aqueous NaCl (5 L). The organic extracts are dried over MgSO$_4$, filtered, and concentrated under reduced pressure to give the title compound as a mixture of diastereomers (8:2) as a dark brown gum (604 g, 91% yield) that may be used without further purification. ES/MS (m/z for $^{79}$Br/$^{81}$Br): 329.0, 331.0 (M+H).

Preparation 7 methyl (2S)-4-amino-2-[(1R)-1-(4-bromophenyl)ethyl]-2-methyl-4-oxo-butanoate and methyl (2R)-4-amino-2-[(1R)-1-(4-bromophenyl)ethyl]-2-methyl-4-oxo-butanoate

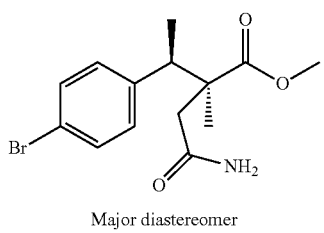

Major diastereomer

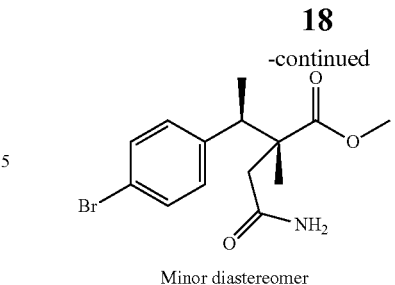

Minor diastereomer

Scheme 1, step G: To a mixture of diastereomers (3R/S,4R)-4-(4-bromophenyl)-3-methoxycarbonyl-3-methylpentanoic acid (603 g, 1282 mmol) and TEA (550 mL, 3870 mmol) in anhydrous DMF (4 L) at 0° C. is added HATU (597 g, 1538.69 mmol) over 15 min. The reaction mixture is aged at RT for 2 hr. A solution of 7 M NH$_3$/MeOH (1.83 L) is added over 30 min at 10° C., and the resulting mixture is warmed to RT and stirred for 1 h. The reaction mixture is cooled to 10° C. and then diluted slowly with DCM (5 L) followed by H$_2$O (5 L). The resulting layers are separated, and the aqueous layer is additionally extracted with DCM (2.5 L). The combined extracts are washed sequentially with H$_2$O (5 L) and saturated aqueous NaCl (5 L), dried over MgSO$_4$, filtered, and concentrated under reduced pressure to give the title compound as a mixture of diastereomers (8:2) as a dark gum (520 g, 87% yield) that may be used without further purification. Major diastereomer t$_R$=0.97 min; minor diastereomer t$_R$=0.99 min (XBRIDGE® C18 column, 3.5 m, 2.1×50 mm, 1.2 mL/min, 50° C., 10-95% 10 mM NH$_4$CO$_3$ (pH 10) in ACN). ES/MS (m/z for $^{79}$Br/$^{81}$Br) 328.0/330.0 (M+H/M+H+2).

Preparation 8

(3S)-3-[(1R)-1-(4-bromophenyl)ethyl]-3-methyl-pyrrolidine-2,5-dione and (3R)-3-[(1R)-1-(4-bromophenyl)ethyl]-3-methyl-pyrrolidine-2,5-dione

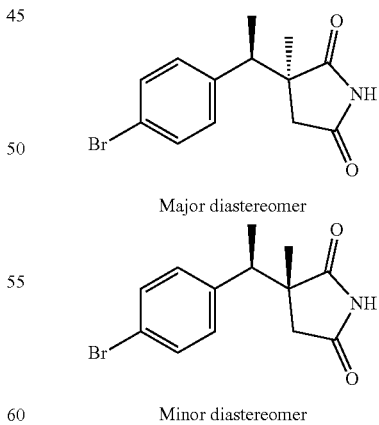

Major diastereomer

Minor diastereomer

Scheme 1, step H: To a mixture of diastereomers methyl (2R/S)-4-amino-2-[(1R)-1-(4-bromophenyl)ethyl]-2-methyl-4-oxo-butanoate (519 g, 1107 mmol) dissolved in THF (4.2 L) and H$_2$O (4.2 L) is added Na$_2$CO$_3$ (293 g, 2764.46 mmol) and the mixture is heated at 60° C. for 2 hr.

The reaction is cooled to RT and extracted with EtOAc (2.5 L). The organic layer is washed with H₂O (3 L). The resulting aqueous extract is extracted with EtOAc (5 L) and the combined organic extracts are dried over MgSO₄, filtered, and concentrated under reduced pressure to give a crude mixture of the two diastereomers that are separated by SFC [Column: AS-H, 150×50 mm; 10% EtOH (0.2% DEMA), 340 g/min; BPR 150 bar; injection volume: 4 ml; 220 nm]. (3R)-3-[(1R)-1-(4-bromophenyl)ethyl]-3-methyl-pyrrolidine-2,5-dione: first eluting compound (43.8 g, 11%). $^1$H NMR (CDCl₃): δ 1.33 (d, J=7.2 Hz, 3H), 1.40 (s, 3H), 2.34 (d, J=18.4 Hz, 1H), 2.80 (, J=18.4 Hz, 1H), 3.23 (q, J=7.2 Hz, 1H), 7.07 (d, 2H), 7.40 (d, 2H), 7.54 (br-s, 1H). ES/MS (m/z for $^{79}$Br/$^{81}$Br): 313.0, 315.0 (M+H). (3S)-3-[(1R)-1-(4-bromophenyl)ethyl]-3-methyl-pyrrolidine-2,5-dione: second eluting compound (241.8 g, 55%). $^1$H NMR (CDCl₃): δ 1.23 (s, 3H), 1.30 (d, J=7.1 Hz, 3H), 2.21 (d, J=18.4 Hz, 1H), 2.96 (d, J=18.4 Hz, 1H), 3.14 (q, J=7.1 Hz, 1H), 7.04-7.09 (m, 2H), 7.42-7.48 (m, 2H), 8.09 (br-s, 1H). ES/MS (m/z for $^{79}$Br/$^{81}$Br): 313.0, 315.0 (M+H).

Preparation 9

2-cyclopropyl-6-methyl-pyridin-4-ol

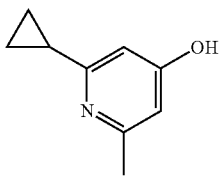

A suspension of NaH (60% in oil, 11.6 g, 289 mmol) in 1,2-dimethoxyethane (150 mL) is heated to 110° C. in an oil bath. A solution of acetylacetone (6.0 mL, 57.8 mmol), methyl cyclopropanecarboxylate (9.0 mL, 86.8 mmol), and 1,2-dimethoxyethane (75 mL) is added dropwise over 40 min. After heating for an additional 4 hr, the suspension is cooled to RT and the DME is removed under reduced pressure. The resulting slurry is diluted with Et₂O (200 mL), cooled in an ice/water bath to about 5° C., and carefully quenched with ice water (200 mL). The layers are separated and the organic layer is washed with water (100 ml) and an aqueous solution of 0.25M NaOH (100 mL). The combined aqueous layers are cooled in an ice/water bath and carefully treated with conc. HCl (40 mL). The acidic aqueous mixture is extracted with Et₂O (4×200 mL), and the organic extracts are dried over Na₂SO₄, filtered, and concentrated under reduced pressure to give a light amber oil. The resulting residue is treated with 28% NH₄OH (180 mL, 4.6 mol) and the resulting mixture is heated to reflux for 3 hr, followed by concentration under reduced pressure. The crude product is purified by flash chromatography on silica, eluting with (2N NH₃/MeOH)/DCM (gradient from 1:99 to 1:9). The pure chromatography fractions are combined and concentrated under reduced pressure to give the title compound (8.0 g, 90% yield). ES/MS (m/z): 150.0 (M+H⁺).

Preparation 10

4-[(1R)-1-[(3S)-3-methyl-2,5-dioxo-pyrrolidin-3-yl]ethyl]benzaldehyde

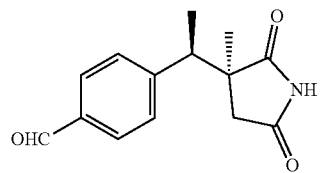 [SMILES: C[C@H](c1ccc(C=O)cc1)[C@]1(C)CC(=O)NC1=O]

Scheme 1, step I: To a 100 ml Parr autoclave is charged (3S)-3-[(1R)-1-(4-bromophenyl)ethyl]-3-methyl-pyrrolidine-2,5-dione (2.47 g, 8.34 mmol), palladium(II) acetate (75 mg, 0.334 mmol), butyldi-1-adamantylphosphine (Cat-aCXium A®) (360 mg, 0.954 mmol), anhydrous toluene (70 ml) and TMEDA (1.3 ml, 8.6 mmol). The autoclave is sealed. The reaction mixture is placed under an atmosphere of synthesis gas (H₂/CO (1:1)) (75 psi), heated to 95° C., and left to stir for 16 h. The mixture is allowed to cool and the suspension is filtered over a pad of diatomaceous earth. The filter cake is washed with EtOAc, and the collected filtrates are concentrated under reduced pressure to afford an amber oil. The crude product is purified by flash chromatography on silica, eluting with hexanes/EtOAc (gradient from 9:1 to 2:3). The pure chromatography fractions are combined and concentrated under reduced pressure to give the title compound (1.27 g, 62% yield). ES/MS (m/z): 263.0 (M+NH₄⁺).

Preparation 11

4-[(1R)-1-[(3S)-3-methyl-2,5-dioxo-1-trityl-pyrrolidin-3-yl]ethyl]benzaldehyde

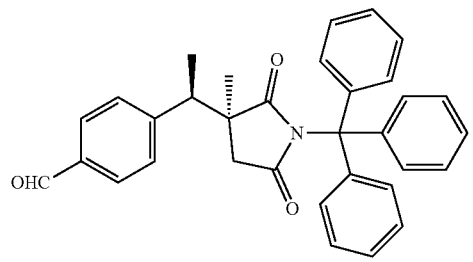 [SMILES: C[C@H](c1ccc(C=O)cc1)[C@]1(C)CC(=O)N(C(c2ccccc2)(c2ccccc2)c2ccccc2)C1=O]

Scheme 1, step J: Cesium carbonate (2.24 g, 6.87 mmol) and triphenylmethyl chloride (1.56 g, 5.50 mmol) are added to a solution of 4-[(1R)-1-[(3S)-3-methyl-2,5-dioxo-pyrrolidin-3-yl]ethyl]benzaldehyde (1.12 g, 4.58 mmol) and DMF (25 ml) stirring at RT. After stirring for 4.5 hr, the mixture is poured into water (100 ml) and extracted with EtOAc (2×75 ml). The combined extracts are washed with water (50 ml) and saturated aqueous NaCl, dried over Na₂SO₄, filtered, and concentrated under reduced pressure, to give a yellow foam. The crude product is purified by flash chromatography on silica, eluting with hexanes/EtOAc (gradient from 49:1 to 7:3). The pure chromatography fractions are Preparation 12

(3S)-3-[(1R)-1-[4-(hydroxymethyl)phenyl]ethyl]-3-methyl-1-trityl-pyrrolidine-2,5-dione

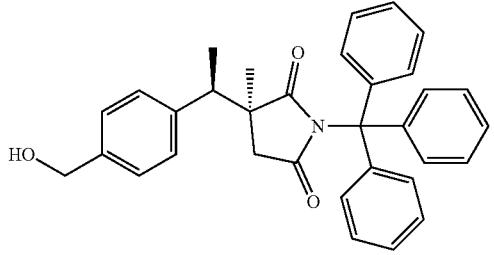 [SMILES: C[C@H](c1ccc(CO)cc1)[C@]1(C)CC(=O)N(C(c2ccccc2)(c2ccccc2)c2ccccc2)C1=O]

Scheme 1, step K: In a single portion, sodium borohydride (147 mg, 3.81 mmol) is added to a suspension of 4-[(1R)-1-[(3S)-3-methyl-2,5-dioxo-1-trityl-pyrrolidin-3-yl]ethyl]benzaldehyde (1.24 g, 2.54 mmol) in EtOH (50 ml), cooled in an ice/water bath. After 40 minutes, the reaction is quenched with water (10 ml) and concentrated under reduced pressure to remove the EtOH. The resulting concentrate is diluted with water (50 ml) and extracted with EtOAc (2×50 ml). The combined extracts are washed with saturated aqueous NaCl, dried over Na$_2$SO$_4$, filtered, and concentrated under reduced pressure to give a white foam. The crude product is purified by flash chromatography on silica, eluting with hexanes/EtOAc (gradient from 19:1 to 1:19). The pure chromatography fractions are combined and concentrated under reduced pressure to give the title compound (1.19 g, 95% yield). ES/MS (m/z): 507.2 (M+NH$_4^+$).

Alternative Procedure to Preparation 12

Sodium borohydride (10 g, 264.3 mmol) is added in 2 g portions to a solution of 4-[(1R)-1-[(3S)-3-methyl-2,5-dioxo-1-trityl-pyrrolidin-3-yl]ethyl]benzaldehyde (160.7 g, 329.6 mmol) dissolved in anhydrous THF (1.6 L) in a 3-necked round bottom flask equipped with an overhead stirrer. The reaction mixture is stirred at RT for 3 hr, diluted with EtAOc (2 L) and water (1.5 L), and the resulting layers are separated. The organic extract is washed sequentially with water (1 L) and saturated aqueous NaCl (500 mL), dried over Na$_2$SO$_4$, filtered, and concentrated under reduced pressure. The resulting residue is dissolved in EtOAc (1 L) and MTBE (1 L), water (500 mL) and aqueous 1N HCl (250 mL) is added, and the biphasic mixture is stirred for about 15 min. The organic layer is separated and washed with saturated aqueous NaCl, dried over Na$_2$SO$_4$, filtered, concentrated under reduced pressure, and the resulting residue is dried in a vacuum oven at 40-50° C. overnight, to obtain the title compound (164.5 g, 96% yield) as a tan solid.

Preparation 13

(3S)-3-[(1R)-1-[4-[(2-cyclopropyl-6-methyl-4-pyridyl)oxymethyl]phenyl]ethyl]-3-methyl-1-trityl-pyrrolidine-2,5-dione

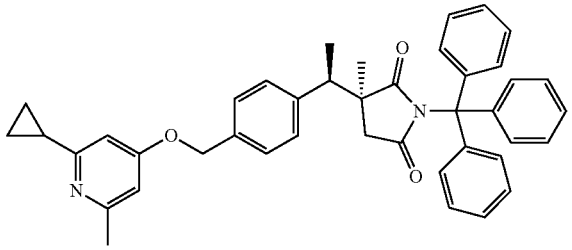 [SMILES: Cc1cc(OCc2ccc([C@@H](C)[C@]3(C)CC(=O)N(C(c4ccccc4)(c4ccccc4)c4ccccc4)C3=O)cc2)cc(C2CC2)n1]

Scheme 1, step L: A solution of (3S)-3-[(1R)-1-[4-(hydroxymethyl)phenyl]ethyl]-3-methyl-1-trityl-pyrrolidine-2,5-dione (636 mg, 1.30 mmol) in DCM (15 mL), cooled to about 5° C. in an ice/water bath, is treated with TEA (274 µL, 1.95 mmol) and methanesulfonyl chloride (122 µL, 1.56 mmol). After stirring in the cold bath for 2 hr, the mixture is diluted with DCM (25 mL) and water (25 mL). The layers are separated and the aqueous is extracted with DCM (25 mL). The combined organic layers are washed with saturated aqueous NaHCO$_3$ and saturated aqueous NaCl, dried over Na$_2$SO$_4$, filtered, and concentrated under reduced pressure, to give crude [4-[(1R)-1-[(3S)-3-methyl-2,5-dioxo-1-trityl-pyrrolidin-3-yl]ethyl]phenyl]methyl methanesulfonate as an oil.

Scheme 1, step M: In a separate flask, added sodium hydride (60% in oil, 78 mg, 1.95 mmol) to a solution of 2-cyclopropyl-6-methyl-pyridin-4-ol (291 mg, 1.95 mmol) in DMF (5 mL). After stirring at RT for 40 minutes, a solution of the crude mesylate in DMF (5 ml) is added to the sodium hydride mixture and stirred at RT for 16 hr. The reaction mixture is quenched with water (50 mL) and extracted with EtOAc (2×50 mL). The combined organic layers are washed with water and saturated aqueous NaCl, dried over Na$_2$SO$_4$, filtered, and concentrated under reduced pressure, to give an oil. The crude product is purified by flash chromatography on silica, eluting with hexanes/EtOAc (gradient from 19:1 to 1:3). The pure chromatography fractions are combined and concentrated under reduced pressure to give the title compound (597 mg, 74% yield). ES/MS (m/z): 621.3 (M+H$^+$).

Alternative Procedure for Preparation 13

A solution of (3S)-3-[(1R)-1-[4-(hydroxymethyl)phenyl]ethyl]-3-methyl-1-trityl-pyrrolidine-2,5-dione (121.3 g, 247.8 mmol) in DCM (1.2 L), cooled to about 5° C. in an ice/water bath, is treated with TEA (52 mL, 373 mmol) and methanesulfonyl chloride (23 mL, 297 mmol) is added dropwise over about 10 min. The reaction mixture is stirred at about 5° C. for about 1 hr, and water (1.2 L) is added. The organic layer is separated and washed with water (500 mL), dried over Na$_2$SO$_4$, filtered, concentrated under reduced pressure, azeotroped with hexane (500 mL), concentrated under reduced pressure, and the resulting residue is subjected to high vacuum, to obtain [4-[(1R)-1-[(3S)-3-methyl-2,5-dioxo-1-trityl-pyrrolidin-3-yl]ethyl]phenyl]methyl methanesulfonate (143.6 g, quantitative yield, product containing hexane) as a yellow solid.

2-Cyclopropyl-6-methyl-pyridin-4-ol (56 g, 375.4 mmol) is dissolved in ACN (1.3 L), and a 2M solution of NaHMDS in THF is added dropwise over 20 min. After complete addition, the reaction mixture is heated to 55° C., and a solution of [4-[(1R)-1-[(3S)-3-methyl-2,5-dioxo-1-trityl-pyrrolidin-3-yl]ethyl]phenyl]methyl methanesulfonate (133.8 g, 235.7 mmol) dissolved in ACN (670 mL) is added dropwise over 45 min at 55° C. The reaction mixture is heated at 55° C. for 1 hr and cooled to RT, poured into a mixture of MTBE (2 L) and water (2 L), and the organic layer is separated, washed with water (500 mL), dried over Na$_2$SO$_4$, filtered, and concentrated under reduced pressure. The resulting residue is dissolved in DCM (300 mL), dried over MgSO$_4$, and filtered over a bed of diatomaceous earth. The filter cake is washed with additional DCM and the filtrate is reduced under reduced pressure. The resulting residue is purified by flash chromatography on silica, eluting with hexanes/acetone (gradient from 9:1 to 7:3). The pure chromatography fractions are combined and concentrated under reduced pressure to give the title compound (62.7 g, 43% yield) as an off-white solid.

Preparation 14

(3S)-3-[(1R)-1-(4-bromophenyl)ethyl]-3-methyl-1-trityl-pyrrolidine-2,5-dione

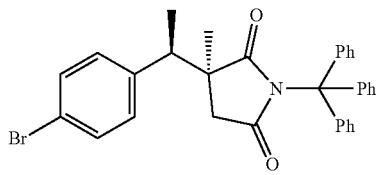 [SMILES: C[C@H](c1ccc(Br)cc1)[C@]1(C)CC(=O)N(C(c2ccccc2)(c2ccccc2)c2ccccc2)C1=O]

Scheme 2, step A: (3S)-3-[(1R)-1-(4-bromophenyl)ethyl]-3-methyl-pyrrolidine-2,5-dione (201 g, 678.6 mmol) is dissolved in DMF (1500 mL) in a 4 L 3-neck flask under nitrogen at RT with mechanical stirring. Cs$_2$CO$_3$ (330 g, 1012.8 mmol) is added over about 5 min, and the mixture is warmed to RT and stirred for an additional 3 hr. The reaction mixture is diluted with water (1500 mL) while maintaining the internal temperature below 20° C. The resulting precipitate is collected by vacuum filtration; the filter cake is washed with water (2×500 mL) and dried under a stream of nitrogen. The filter cake is transferred to a 12 L 3-neck with mechanical stirring. MeOH (4 L) is added, and the mixture is heated to reflux for about 5 min. The methanolic solution is cooled to about 0° C., the resulting precipitate is collected by vacuum filtration, and the solids are dried at about 50° C. under vacuum to obtain the title compound (350.9 g, 96% yield) as a white solid. ES/MS (m/z, $^{79}$Br/$^{81}$Br): 538.1/540.1 (M+H$^+$).

Preparation 15

4-[(1R)-1-[(3S)-3-methyl-2,5-dioxo-1-trityl-pyrrolidin-3-yl]ethyl]benzaldehyde

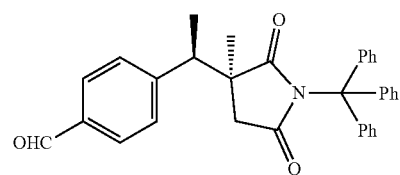 [SMILES: C[C@H](c1ccc(C=O)cc1)[C@]1(C)CC(=O)N(C(c2ccccc2)(c2ccccc2)c2ccccc2)C1=O]

Scheme 2, step B: (3S)-3-[(1R)-1-(4-bromophenyl)ethyl]-3-methyl-pyrrolidine-2,5-dione (185.5 g, 0.35 mol) is divided into 3 equal portions and each is placed into a Parr autoclave vessel, each containing palladium(II) acetate (0.77 g, 3.4 mmol), butyldi-1-adamantylphosphine (CataCXium A®) (5.0 g, 0.014 mol), anhydrous toluene (500 ml) and TMEDA (17.5 ml, 0.12 mol). Each vessel is evacuated and filled to about 75 psi with an atmosphere of CO/H$_2$. The vessels are heated at 95° C. for 16 hr and cooled to RT. Each reaction is filtered over a bed of diatomaceous earth, and the filtrates are combined and concentrated under reduced pressure. The resulting residue is dissolved in toluene (~1 L), transferred to a 2 L 3-neck flask, activated charcoal (200 g (200 g of) is added, and the mixture is stirred at RT overnight. The reaction mixture is filtered over a bed of diatomaceous earth, the filter cake is washed with MTBE (1 L), and the filtrate is concentrated under reduced pressure. The resulting residue is slurried in EtOH (1.3 L), heated to 75° C., and water (640 mL) is added dropwise over ~20 min. The mixture is cooled to RT and the solids are collected by filtration, rinsed with water (500 mL), and dried under a nitrogen press, to obtain the title compound (160.7 g, 87% yield) as a yellow solid. ES/MS (m/z): 488.1 (M+H$^+$).

Example 1

(3S)-3-[(1R)-1-[4-[(2-cyclopropyl-6-methyl-4-pyridyl)oxymethyl]phenyl]ethyl]-3-methyl-pyrrolidine-2,5-dione

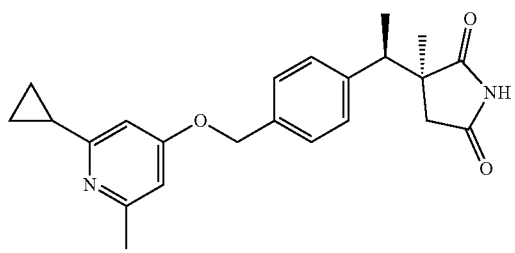 [SMILES: Cc1cc(OCc2ccc([C@@H](C)[C@]3(C)CC(=O)NC3=O)cc2)cc(C2CC2)n1]

Scheme 1, step N: To a solution of (3S)-3-[(1R)-1-[4-[(2-cyclopropyl-6-methyl-4-pyridyl)oxymethyl]phenyl]ethyl]-3-methyl-1-trityl-pyrrolidine-2,5-dione (597 mg, 0.961 mmol) in DCM (5 ml) is added TFA (3 ml, 38.6 mmol) and the mixture is stirred for 17 hr. After concentrating under reduced pressure, added DCM (20 ml) and water (20 ml) to the concentrate, and adjusted to pH 6 with 1N aqueous NaOH. Extracted with DCM (2×50 ml), dried over $Na_2SO_4$, filtered, and concentrated under reduced pressure, to give an oil. The crude product is purified by flash chromatography on silica, eluting with DCM/MeOH (gradient from 1:0 to 9:1). The pure chromatography fractions are combined and concentrated under reduced pressure to give the title compound (332 mg, 91% yield). ES/MS (m/z): 379.0 (M+H$^+$). $[\alpha]_D^{20}$=−42.142° (C=0.2, MeOH)

Alternative Procedure for Example 1

(3S)-3-[(1R)-1-[4-[(2-cyclopropyl-6-methyl-4-pyridyl) oxymethyl]phenyl]ethyl]-3-methyl-1-trityl-pyrrolidine-2,5-dione (61.7 g, 99.4 mmol) is dissolved in DCM (230 mL) and cooled to about 5° C. TFA (310 mL) is added slowly over about 10 min, the reaction mixture is warmed to RT, and stirred overnight. The reaction mixture is concentrated under reduced pressure and the resulting residue is partitioned between MTBE (620 mL) and water (620 mL). The mixture is cooled to about 5° C., an aqueous solution of 5N NaOH is added (pH 14), and the layers are separated. The aqueous extract is acidified with conc. HCl (pH~5) and extracted with EtOAc (1.2 L). The layers are separated, the organic extracts are washed with saturated aqueous NaHCO$_3$ (2×500 mL), dried over MgSO$_4$, filtered, concentrated under reduced pressure, and subjected to high vacuum for about 2 hr to obtain the title compound (31.4 g, 83.5% yield) as an off-white solid. ES/MS (m/z): 379.0 (M+H$^+$).

Example 1A (3S)-3-[(1R)-1-[4-[(2-cyclopropyl-6-methyl-4-pyridyl)oxymethyl]phenyl]ethyl]-3-methyl-pyrrolidine-2,5-dione Hydrobromide Monohydrate

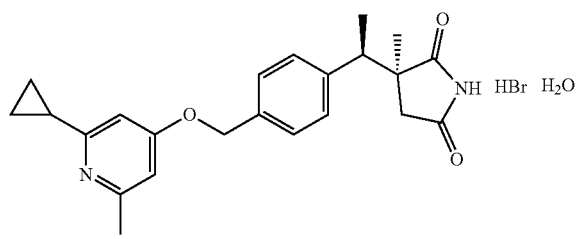 [SMILES: Cc1cc(OCc2ccc([C@@H](C)[C@]3(C)CC(=O)NC3=O)cc2)cc(C2CC2)n1 ; Cl ; O]

(3S)-3-[(1R)-1-[4-[(2-cyclopropyl-6-methyl-4-pyridyl) oxymethyl]phenyl]ethyl]-3-methyl-pyrrolidine-2,5-dione (401 mg, 1.06 mmol) is slurried in EtOAc (8 mL) at 60° C. A solution of 48% hydrobromic acid dissolved in EtOAc (2 mL) is added, and the mixture is stirred at 60° C. for 1 h. The resulting white solid is collected by filtration, rinsed with EtOAc, and air dried, to obtain the title compound (385 mg, 79% yield) as a white crystalline solid.

Example 1B (3S)-3-[(1R)-1-[4-[(2-cyclopropyl-6-methyl-4-pyridyl)oxymethyl]phenyl]ethyl]-3-methyl-pyrrolidine-2,5-dione Hydrochloride Monohydrate

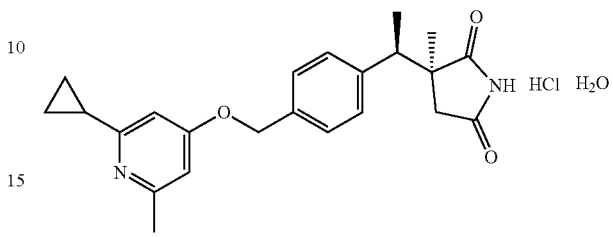

(3S)-3-[(1R)-1-[4-[(2-cyclopropyl-6-methyl-4-pyridyl) oxymethyl]phenyl]ethyl]-3-methyl-pyrrolidine-2,5-dione (250 mg, 0.7 mmol) is dissolved in a mixture of EtOAc/ EtOH (4:1) with stirring at 60° C. A solution of 1 M HCl in EtOAc (0.7 mL) is added, and the resulting mixture is stirred at 60° C. for 1 h, cooled to RT, an d the light yellow precipitate is collected by filtration, rinsed with EtOAc, and air dried to obtain the title compound (151 mg, 55% yield) as a light yellow crystalline solid.

X-Ray Powder Diffraction (XRPD)

The XRPD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2θ.

A sample of compound of Example 1A is characterized by an XRD pattern using CuKa radiation as having diffraction peaks (2θ values) as described in Table 1 below. Specifically the pattern contains a peak at 26.1° in combination with one or more of the peaks selected from the group consisting of 13.9°, 22.1°, 8.7°, 19.5°, and 18.8° with a tolerance for the diffraction angles of ±0.2 degrees.

TABLE 1

X-ray powder diffraction peaks of crystalline compound of Example 1A; (3S)-3-[(1R)-1-[4-[(2-cyclopropyl-6-methyl-4-pyridyl)oxymethyl]phenyl]ethyl]-3-methyl-pyrrolidine-2,5-dione hydrobromide monohydrate

| Peak | Angle (°2θ +/− 0.2) | Relative Intensity (% of most intense peak) |
|---|---|---|
| 1 | 26.1 | 100 |
| 2 | 13.9 | 95 |
| 3 | 22.1 | 53 |
| 4 | 8.7 | 32 |
| 5 | 19.5 | 23 |
| 6 | 18.8 | 22 |
| 7 | 20.2 | 22 |
| 8 | 14.4 | 21 |
| 9 | 21.3 | 20 |
| 10 | 17.9 | 18 |

A sample of compound of Example 1B is characterized by an XRD pattern using CuKa radiation as having diffraction peaks (2θ values) as described in Table 2 below. Specifically the pattern contains a peak at 26.3° in combination with one or more of the peaks selected from the group consisting of 13.8°, 22.2°, 19.7°, 21.3°, 14.1°, and 25.4° with a tolerance for the diffraction angles of ±0.2 degrees.

TABLE 2

X-ray powder diffraction peaks of crystalline compound of Example 1B; (3S)-3-[(1R)-1-[4-[(2-cyclopropyl-6-methyl-4-pyridyl)oxymethyl]phenyl]ethyl]-3-methyl-pyrrolidine-2,5-dione hydrochloride monohydrate.

| Peak | Angle (°2θ +/− 0.2) | Relative Intensity (% of most intense peak) |
|---|---|---|
| 1 | 26.3 | 100 |
| 2 | 13.8 | 97 |
| 3 | 22.2 | 47 |
| 4 | 19.7 | 34 |
| 5 | 21.3 | 31 |
| 6 | 14.1 | 30 |
| 7 | 25.4 | 25 |
| 8 | 14.5 | 22 |
| 9 | 28.1 | 19 |
| 10 | 20.2 | 18 |

Inhibition of cAMP Production by CGRP Receptor Antagonists

The hCGRP (human calcitonin gene-related peptide) receptor is functionally coupled to the Gas proteins. Stimulation of hCGRP results in an increased synthesis of intracellular cAMP and can be blocked by the addition of receptor antagonists. Receptor activity is thus a reflection of the amount of cAMP present within cells which can be detected using standard in vitro technology.

Cell Culture:

Cultured SK-N-MC neuroblastoma cells that endogenously express the hCGRP receptor (ATCC) are grown in Eagle's Minimum essential medium (HYCLONE™) supplemented with 10% heat-inactivated Fetal bovine serum (FBS; GIBCO®), Non-Essential Amino Acids (GIBCO®), 1 mM sodium pyruvate, 2 mM L-glutamine, 100 U/mL of penicillin, and 10 µg/mL of streptomycin to about 70% confluency. After providing fresh medium, the cells are incubated at 37° C. overnight. On the day of the assay, cells are detached using ACCUTASE® (MP Biomedicals), resuspended in assay buffer [Hank's Balanced Salt Solution/Dulbecco's phosphate-buffered saline with 100 mg/mL each of $CaCl_2$) and $MgCl_2$ mixed 1:2, 3.3 mM 4-(2-hydroxyethyl)-1-piperazineethanesulfonic acid, 0.03% bovine serum albumin, and 0.5 mM 1-methyl-3-isobutylxanthine (as inhibitor of cAMP)], and seeded 3-5K/well into 384-well, poly-D-lysine coated white plates (BD Biosciences).

Inhibition of cAMP Production:

For dose-response studies, compounds are serially diluted 1:3 in dimethyl sulfoxide and then 1:10 into assay buffer. Human CGRP (0.8 nM; Bachem) as a receptor-specific agonist for the hCGRP receptor is mixed with diluted compound and added to the cells as the challenge stimulant at their $EC_{80}$ concentrations.

Data Analysis:

The amount of intracellular cAMP is quantitated using HTRF technology (Cisbio) as per vendor instructions. Briefly, cAMP-d2 conjugate and anti-cAMP-cryptate conjugate in lysis buffer are incubated with the treated cells at RT for 90 min. The HTRF signal is immediately detected using an ENVISION® plate reader (Perkin-Elmer) to calculate the ratio of fluorescence at 665 to 620 nM. The raw data are converted to cAMP amount (pmole/well) using a cAMP standard curve generated for each experiment. Relative $EC_{50}$ values are calculated from the top-bottom range of the concentration response curve using a four-parameter logistic curve fitting program (ACTIVITYBASE® v5.3.1.22 or GENEDATA SCREENER® v12.0.4), and $K_b$ values are estimated as agonist-corrected $IC_{50}$ values using the equation:

$$K_b=(IC_{50})/[1+([Agonist]/EC_{50})].$$

Estimated $K_b$ values are reported as mean values±SEM, averaged from the number of runs (n).

Following the procedure essentially as described above, compound of Example 1 has a $K_b$ measured at human CGRP of 0.57±0.25 nM (n=11). This demonstrates that the compound of Example 1 is an antagonist of the human CGRP receptor in vitro.

In Vitro Determination of Efflux by ABCB1, Human P-Glycoprotein (Pgp)

Cell Culture:

MDCKII cells stably expressing human wild-type ABCB1 (Pgp) are obtained from the Netherlands Cancer Institute (Amsterdam, The Netherlands). MDCK cells are maintained as described previously (Desai et al., Mol Pharm 10:1249-1261, 2013).

Bi-Directional Transport Across MDCK Cells:

The assay is essentially conducted as described previously (Desai et al., Mol Pharm 10:1249-1261, 2013). Transport is measured in both directions across uninhibited and inhibited cell monolayers using a substrate concentration of 5 µM diluted from a 10 mM DMSO stock solution (final DMSO concentration of 0.05%) and a single 60-min time interval. 2.5 µM of the compound of Example 1 is used to selectively inhibit Pgp. The apparent permeability coefficients (Papp) are estimated as the slope of the mass transported per 60 min relative to the total recovered mass. The basal-to-apical (B-A)/apical-to-basal (A-B) Papp ratios are calculated in the absence or presence of inhibitor in each cell line for net efflux ratio (NER). The NER of the compound of Example 1 for efflux by Pgp is determined to be 1.7.

In Vivo Determination of Unbound Brain-to-Plasma Partition Coefficient ($K_{p,uu,brain}$) in Rats Unbound brain-to-plasma partition coefficient ($K_{p,uu,brain}$) is one of the key pharmacokinetic parameter for evaluating a compound's ability to cross the blood-brain barrier (BBB) (Hammarlund-Udenaes, M.; Friden, M.; Syvanen, S.; Gupta, A. On the Rate and Extent of Drug Delivery to the Brain. *Pharm. Res.* 2008, 25 (8), 1737-1750). $K_{p,uu,brain}$ is typically measured in pre-clinical species using the following methodology, and $K_{p,uu,brain}$ values exceeding 0.3 suggest that more than 30% of the unbound compound in plasma crosses the BBB.

Study Populations:

Animal studies are performed under protocols approved by the Covance Institutional Animal Care and Use Committee. Male Sprague-Dawley rats weighing 250-350 g are obtained from Harlan Sprague Dawley Inc. (Indianapolis, Ind.). Animals have access to food and water ad libitum before and during the study.

Dose Administration:

Animals each receive 10 mg/kg of the CGRP receptor antagonist compound of Example 1, administered orally in 10 ml/kg of hydroxyethylcellulose 1% w/v/polysorbate 80 0.25% v/v/Antifoam 1510-US 0.05% v/v/in purified water (probe sonicated).

Pharmacokinetic Sampling:

Three animals per time point are used. The blood (by cardiac puncture) and brain samples are collected at 0.5 and 2 h post dose. The blood samples are treated with $K_3$-EDTA anticoagulant, and plasma is obtained by centrifugation at 1600 g for 10 minutes. The brain samples are weighed and homogenized, without perfusion. All samples are stored at −70° C. until analysis by LC-MS/MS to determine the concentration of the compound of Example 1 in plasma and brain at each time point.

Determination of Plasma and Brain Protein Binding:

Rat plasma and brain homogenate protein in vitro binding is determined using equilibrium dialysis, as described elsewhere [Zamek-Gliszczynski et al., J Pharm Sci, 101:1932-1940, 2012]. The results are reported as fraction unbound in plasma ($f_{u,plasma}$) and brain ($f_{u,brain}$), which are then utilized to calculate $K_{p,uu,brain}$, as described in Table 1. Rat $f_{u,plasma}$ and $f_{u,brain}$ of the compound of Example 1 are determined to be 0.071 and 0.043, respectively.

Analysis and Results:

$K_{p,uu,brain}$ is calculated for each time point from the expression below where individual components are derived from a combination of in vitro and in vivo measurements carried out as described above:

$$K_{p,uu,brain} = \frac{C_{u,brain}}{C_{u,plasma}} = \frac{C_{total,brain}}{C_{total,plasma}} \cdot \frac{f_{u,brain}}{f_{u,plasma}}$$

where $C_{total,brain}$, $C_{u,brain}$, $C_{total,plasma}$ and $C_{u,plasma}$ are total and unbound brain and plasma concentrations, and $f_{u,brain}$ and $f_{u,plasma}$ are fractions unbound in brain and plasma, respectively.

The plasma and brain concentrations for the compound of Example 1 are provided in Table 3. The results are expressed as mean±standard deviation.

TABLE 3

Plasma and brain concentrations of compound of Example 1 post 10 mg/kg oral dose in male Sprague-Dawley rats. The results are expressed as mean ± standard deviation.

| Time point (hr) | Total brain conc. ($C_{total, brain}$) (nM) | Total plasma conc. ($C_{total, plasma}$) (nM) | Unbound brain conc. ($C_{u, brain}$) (nM)* | Unbound plasma conc. ($C_{u, plasma}$) (nM) | $K_{p, uu, brain}$ |
|---|---|---|---|---|---|
| 1.0 | 962 ± 341 | 655 ± 183 | 41 ± 15 | 47 ± 13 | 0.89 ± 0.17 |
| 3.0 | 515 ± 111 | 368 ± 127 | 22 ± 5 | 26 ± 9 | 0.93 ± 0.43 |

*Using rat $f_{u, brain}$ value of 0.043 and ^rat $f_{u, plasma}$ value of 0.071, as described above.

The unbound brain concentrations of Example 1 at 1 and 3 hours post oral dose of 10 mpk in male Sprague-Dawley rats are determined to be 41±15 nM and 22±5 nM, respectively. In addition, $K_{p,uu,brain}$ of Example 1 at 1 and 3 hours post oral dose of 10 mpk in male Sprague-Dawley rats is determined to be 0.89±0.17 and 0.93±0.43, respectively. Taken in their entirety, these data indicate that the compound of Example 1 is a centrally-penetrant compound.

We claim:

1. A compound of the formula:

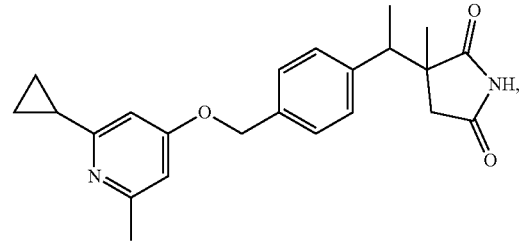 [SMILES: Cc1cc(OCc2ccc(C(C)C3(C)CC(=O)NC3=O)cc2)cc(C2CC2)n1]

or a pharmaceutically acceptable salt or hydrate thereof.

2. The compound or salt according to claim 1 of the formula:

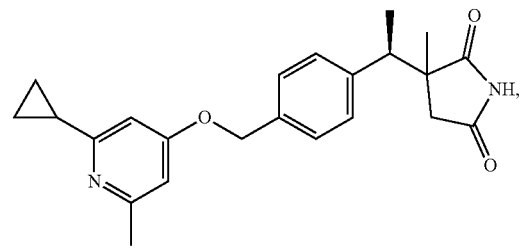 [SMILES: Cc1cc(OCc2ccc([C@@H](C)C3(C)CC(=O)NC3=O)cc2)cc(C2CC2)n1]

or hydrate thereof.

3. The compound or salt according to claim 2 of the formula:

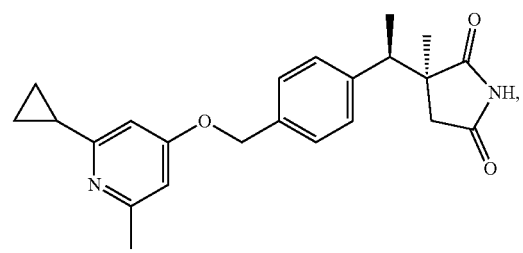 [SMILES: Cc1cc(OCc2ccc([C@@H](C)[C@]3(C)CC(=O)NC3=O)cc2)cc(C2CC2)n1]

or hydrate thereof.

4. The compound or salt according to claim 3 which is:

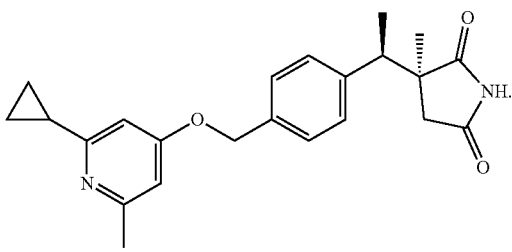

5. The compound according to claim 4 which is:

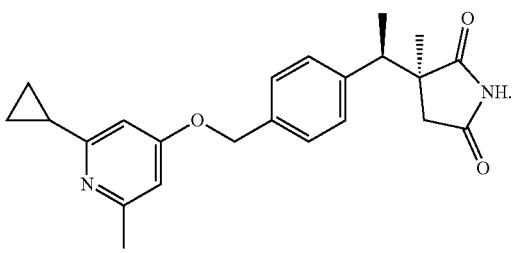 [SMILES: Cc1cc(OCc2ccc([C@@H](C)[C@]3(C)CC(=O)NC3=O)cc2)cc(C2CC2)n1]

6. The compound according to claim 1 which is (3S)-3-[(1R)-1-[4-[(2-cyclopropyl-6-methyl-4-pyridyl)oxymethyl]phenyl]ethyl]-3-methyl-pyrrolidine-2,5-dione hydrochloride, or hydrate thereof.

7. The compound according to claim 6 which is (3S)-3-[(1R)-1-[4-[(2-cyclopropyl-6-methyl-4-pyridyl)oxymethyl]phenyl]ethyl]-3-methyl-pyrrolidine-2,5-dione hydrochloride monohydrate.

8. The compound according to claim 7 wherein the compound is crystalline.

9. The compound according to claim 8 which is characterized by a peak in the X-ray powder diffraction spectrum at diffraction angle 2-theta of 26.3° in combination with one or more peaks selected from the group consisting of 13.8°, 22.2°, 19.7°, 21.3°, 14.1°, and 25.4°, with a tolerance for the diffraction angles of 0.2 degrees.

10. The compound according to claim 1 which is (3S)-3-[(1R)-1-[4-[(2-cyclopropyl-6-methyl-4-pyridyl)oxymethyl]phenyl]ethyl]-3-methyl-pyrrolidine-2,5-dione hydrobromide, or hydrate thereof.

11. The compound according to claim 10 which is (3S)-3-[(1R)-1-[4-[(2-cyclopropyl-6-methyl-4-pyridyl)oxymethyl]phenyl]ethyl]-3-methyl-pyrrolidine-2,5-dione hydrobromide monohydrate.

12. The compound according to claim 11 wherein the compound is crystalline.

13. The compound according to claim 12 which is characterized by a peak in the X-ray powder diffraction spectrum at diffraction angle 2-theta of 26.1° in combination with one or more peaks selected from the group consisting of 13.9°, 22.1°, 8.7°, 19.5°, 18.8°, with a tolerance for the diffraction angles of 0.2 degrees.

14. A pharmaceutical composition, comprising a compound or salt, or hydrate thereof, according to claim 1 with one or more pharmaceutically acceptable carriers, diluents, or excipients.

15. A pharmaceutical composition, comprising a compound or salt, or hydrate thereof, according to claim 3 with one or more pharmaceutically acceptable carriers, diluents, or excipients.

16. A process for preparing a pharmaceutical composition, comprising admixing a compound or salt, or hydrate thereof, according to claim 1 with one or more pharmaceutically acceptable carriers, diluents, or excipients.

17. A process for preparing a pharmaceutical composition, comprising admixing a compound or salt, or hydrate thereof, according to claim 3 with one or more pharmaceutically acceptable carriers, diluents, or excipients.

18. A method of treating migraine in a patient, comprising administering to a patient in need thereof an effective amount of a compound or salt, or hydrate thereof, according to claim 1.

19. A method of treating migraine in a patient, comprising administering to a patient in need thereof an effective amount of a compound or salt, or hydrate thereof, according to claim 3.

* * * * *